United States Patent [19]

Salek

[11] Patent Number: 4,938,756

[45] Date of Patent: Jul. 3, 1990

[54] AUXILIARY ABSORBENT ARTICLE

[75] Inventor: Joann E. Salek, Somerville, N.J.

[73] Assignee: Chicopee, New Brunswick, N.J.

[21] Appl. No.: 805,243

[22] Filed: Dec. 3, 1985

Related U.S. Application Data

[63] Continuation of Ser. No. 521,818, Aug. 10, 1983, abandoned.

[51] Int. Cl.$^5$ .............................................. A61F 13/16
[52] U.S. Cl. ..................................... 604/368; 604/378; 604/401
[58] Field of Search ............... 604/386, 387, 389, 393, 604/394, 395, 396, 397, 398–402, 385.1, 385.2, 368, 378

[56] References Cited

U.S. PATENT DOCUMENTS 3,654,929  4/1972  Nilsson et al. ..................... 604/368
3,886,941  6/1975  Duane et al. ...................... 604/368
3,981,306  9/1976  Krusko ............................. 604/368
4,055,180  10/1977  Karami ........................... 604/378
4,269,188  5/1981  Nishizawa et al. ................ 604/368

Primary Examiner—C. Fred Rosenbaum
Assistant Examiner—Sharon Rose
Attorney, Agent, or Firm—Lawrence D. Schuler

[57] ABSTRACT

An auxiliary absorbent article for use atop a primary absorbent article such as a diaper, said auxiliary absorbent article comprising an upper facing layer, a superabsorbent layer and an undersurface, said superabsorbent layer comprising a superabsorbent material dispersed at a matrix such that fluid passes through said auxiliary absorbent article and may be absorbed by the primary absorbent article and subsequently absorbed by the auxiliary absorbent article in the regions remote from the initial wetting.

6 Claims, 2 Drawing Sheets

FIG-2

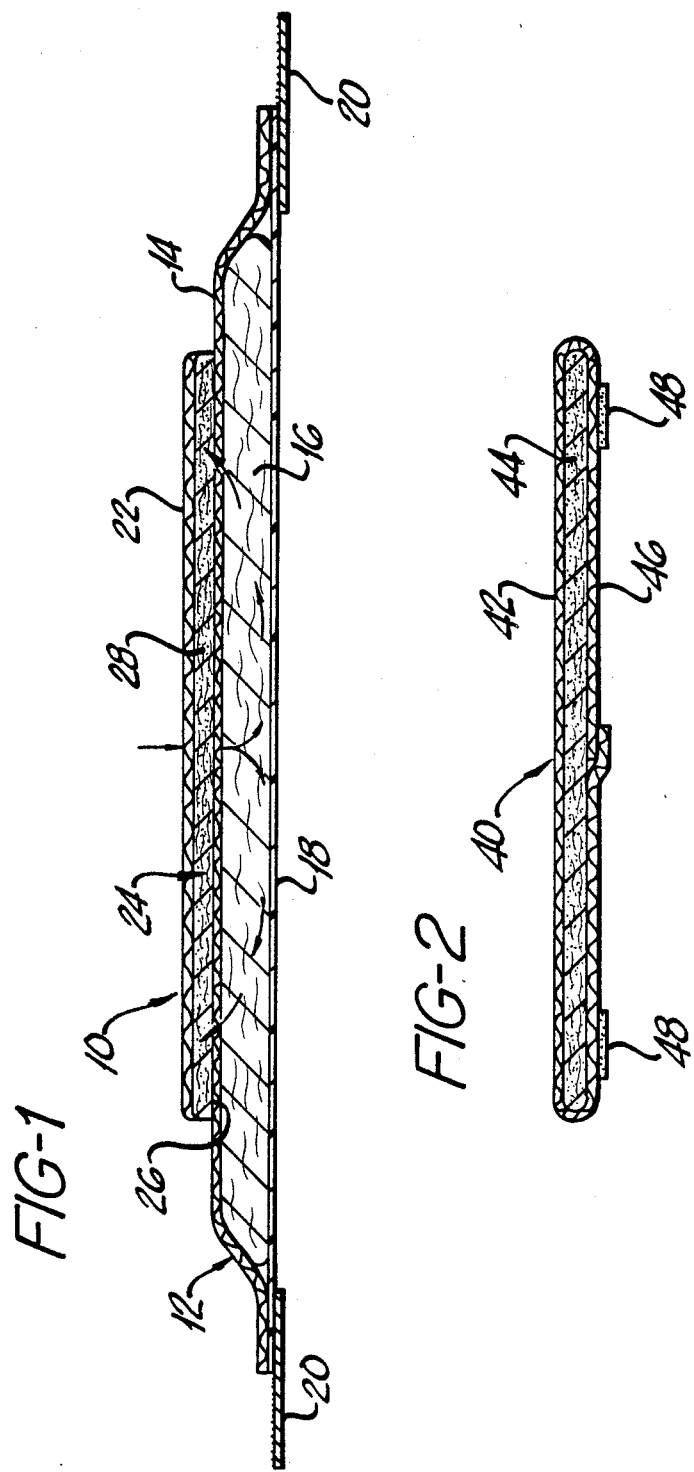

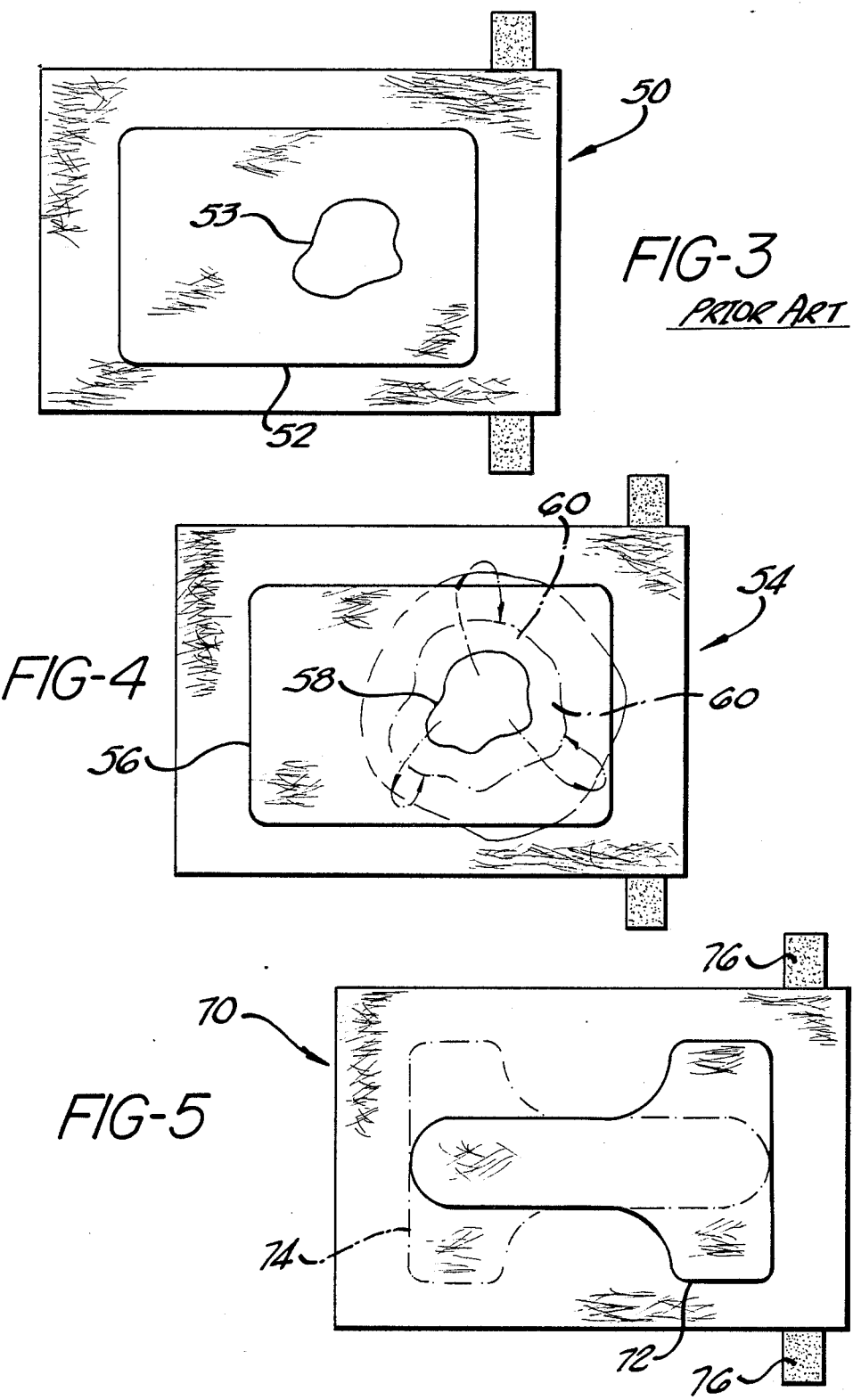

AUXILIARY ABSORBENT ARTICLE

This is a continuation, of application Ser. No. 521,818, filed Aug. 10, 1983, now abandoned.

BACKGROUND OF THE INVENTION

Various auxiliary absorbent articles for use, e.g., with disposable diapers are currently being manufactured and sold. Most of these auxiliary absorbent articles, commonly called booster pads, comprise wood pulp pads with various facing layers. For example Weyerhaeuser manufactures the Revco Diaper Doubler, comprising a 100% wood pulp pad with a polyester facing and a bulk of 220 mils, as well as a booster pad comprising a 100% wood pulp pad with a rayon facing and a bulk of 323 mils. Though both of these booster pads have absorbent capacity and wicking ability, the absorbent capacity is achieved at the expense of the bulk of the pad, and the high degree of absorption by the booster pad holds fluid from the diaper. The bulk of these commercially available pads may be contrasted to the approximate 70 to 130 mils of the auxiliary absorbent article of the present invention.

U.S. Pat. No. 3,886,941 describes a booster pad containing superabsorbent material and an elaborate construction for the facing or bottom sheet involving valves formed by embossing or dimpling a slit sheet of fluid impermeable material into the pad. This booster pad construction is alleged to have a high degree of initial absorption and wicking properties. This booster pad construction has not been commercialized and booster pad constructions in general containing superabsorbent materials have had the disadvantage that when initially wetted the superabsorbent material swells quickly and blocks the further absorption of fluid as the superabsorbent is unable to wick the fluid further or allow it through the block. Copending application (CHIC-666) describes an absorbent article containing superabsorbent layers provided with an internal wicking means to move the fluid to the superabsorbent layers.

SUMMARY OF THE INVENTION

The present invention comprises an auxiliary absorbent article for use in conjunction with a a primary absorbent article such as a diaper. The auxiliary absorbent article comprises an upper facing layer, a superabsorbent layer and an undersurface. The superabsorbent layer comprises a superabsorbent material dispersed in a matrix such that fluid passes the auxiliary absorbent article and may be absorbed by the primary absorbent article. The auxiliary absorbent article adds to the absorbent capacity of the primary absorbent article while adding a minimum of bulk and does not interfere with the absorption by the primary absorbent article by allowing fluid to flow through the superabsorbent layer and by using the wicking ability of the primary absorbent article to move the fluid to remote regions from the initial wetting of the auxiliary absorbent article. The auxiliary absorbent article may be provided with intermittent adhesive along the undersurface thereof for fastening to the primary absorbent article. In the preferred construction, the facing layer encircles the superabsorbent layer and forms the undersurface of the auxiliary absorbent article. In another preferred embodiment, the superabsorbent layer comprises superabsorbent material in a tissue layer. The auxiliary absorbent article may be rectangular, or in a preferred embodiment may be T-shaped.

BRIEF DESCRIPTION OF THE DRAWINGS

FIG. 1 is a cross-sectional view of the auxiliary absorbent article according to the present invention atop a primary absorbent article, a diaper.

FIG. 2 is a cross-sectional view of a preferred embodiment of the auxiliary absorbent article of the present invention.

FIG. 3 is a schematic of a top plan view of a prior art booster pad disposed on a diaper.

FIG. 4 is a schematic of a top plan view of an auxiliary absorbent article according to the present invention disposed on a diaper.

FIG. 5 is a schematic of a top plan view of another embodiment of the auxiliary absorbent article of the present invention disposed on a diaper.

DETAILED DESCRIPTION OF THE INVENTION

FIG. 1 discloses an auxiliary absorbent article according to the present invention shown generally at 10 as used atop a primary absorbent article such as a diaper shown generally at 12. The diaper comprises a facing layer 14, an absorbent pad 16, a backing layer 18 and tape tabs 20. The auxiliary absorbent article comprises a facing layer 22, a superabsorbent layer 24 and an undersurface 26. In use the auxiliary absorbent article is placed atop the primary absorbent article bringing the undersurface 26 of the auxiliary absorbent article in contact with the facing or upper surface of the diaper. The facing layer 22 of the auxiliary absorbent article may comprise any moisture-pervious nonwoven fabric, including carded, random-laid or spunbond fibers of 100% polyester, rayon, polypropylene fibers or blends thereof, or a combination of wood pulp and fusible fibers such as described in U.S.S.N. 382,731. The superabsorbent layer 24 comprises a superabsorbent material dispersed in a matrix such that fluid passes through the auxiliary absorbent article to the primary absorbent article. This is accomplished by well dispersing small particles of superabsorbent material in the matrix. The auxiliary absorbent article makes use of the wicking ability of the primary absorbent article and therefore requires little wicking ability of its own. In use fluid passes through the auxiliary absorbent article at least on first wetting and is wicked by the primary absorbent article to remote regions 28 where it may be absorbed by the superabsorbent layer of the auxiliary absorbent article. This is to be contrasted to most uses of superabsorbents where fluid is brought to the area of the superabsorbent, is absorbed, and stays there. In the auxiliary absorbent article of the present invention, the superabsorbent material throughout the superabsorbent layer may be utilized even if the superabsorbent layer has little inherent wicking ability. In addition by letting fluid pass initially through the superabsorbent layer into the primary absorbent article, the auxiliary absorbent article of the present invention uses the absorbent capacity and wicking properties of the primary absorbent article to not only move fluid but to allow time for the superabsorbent material to swell. The auxiliary absorbent article of the present invention is easy to construct, inexpensive to manufacture and may be made from commercially available materials. One such material for use as a superabsorbent layer is the Akucell fabric, an air laid nonwoven comprising wood pulp and particulate superabsorbent manufactured by Akzo. By using superabsorbent materials, the auxiliary absorbent article of the present invention can be made with much less bulk and weight than traditional booster pads comprising wood pulp. In addition superabsorbent materials are superior to wood pulp pads in that they retain fluid well under pressure and don't break up in the manner of pulp pads or panels.

FIG. 2 discloses a preferred embodiment of the auxiliary absorbent article of the present invention shown generally at 40. In this embodiment the facing layer 42 encircles the superabsorbent layer 44 thereby forming the undersurface 46 of the auxiliary absorbent article. This auxiliary absorbent article is also provided with intermittent adhesive 48 on the undersurface for fastening to the upper surface or facing layer of the primary absorbent article.

In the chart below the auxiliary absorbent article of the present invention is compared to the booster pads currently available on the market. Each of the booster pads was tested in conjunction with a commercially available diaper and the figures for the absorbent capacity and leakage of the diaper alone comprise an average of three samples of the commercially available diaper. The figures for the Revco Diaper Doublers comprise an average of two test trials with the same commercially available diaper. The figures for the auxiliary absorbent article of the present invention comprise an average of two samples of auxiliary absorbent article, also tested in conjunction with the commercially available diaper, wherein the superabsorbent layer comprised two plies of Akucell.

In the test method used, the diaper or diaper with booster pad is fastened in place on a life-size doll constructed so as to be able to void into the diaper to simulate actual use. The test liquid is a 1.59 percent saline solution containing a red dye. The test solution is poured through the doll into the diaper in 90 mil. increments, with a ten minute wait between increments. The test is stopped at the first indication of a leak of the liquid out of the diaper. The test is carried out with the doll placed on an absorbent underpad of known weight so that the amount of leaked fluid can be determined. The diapers and booster pads are also weighed before and after the tests so that the amount of liquid absorbed by the diaper or booster pad can be determined.

present invention allow the underlying absorbent article or diaper to achieve its full absorbent capacity as contrasted with conventional booster pads which absorb immediately and prevent the underlying diaper from achieving its full absorbent capacity.

Though the superabsorbent layer in the above tested auxiliary absorbent article comprised two plies of an Akucell fabric, other commercially available products may be used to form the superabsorbent layer, such as the Henkel superabsorbent fibrous layer and the Dow laminate. In constructing this superabsorbent layer of the auxiliary absorbent article of the present invention, it is necessary only that the superabsorbent material be well dispersed so that the fluid passes through the auxiliary absorbent article on initial wetting.

FIG. 3 shows a schematic representation of observation made while testing the commercial Revco Diaper Doublers in conjunction with the commercial diaper, the results of which are set forth in the Table. In FIG. 3, the commercial diaper is represented at 50 and the Revco Diaper Doubler at 52. When the booster pad and diaper were observed following the introduction and absorption of each increment of fluid, it was noted that the fluid 53 was absorbed by the booster pad and wicked through the booster pad as shown by the arrow. It may be assumed that fluid was absorbed by the diaper from the undersurface of the booster pad.

The absorption dynamics of the booster pad and diaper may be contrasted with that observed with the auxiliary absorbent article of the present invention and the commercial diaper, set out schematically in FIG. 4. In FIG. 4, the commercially available diaper is represented at 54 and the auxiliary absorbent article shown generally at 56. As was observed in connection with the use of the auxiliary absorbent article according to the present invention, the area of initial wetting 58 in FIG. 4 remained small. While the area of initial wetting remained small, it was noted that the fluid was being rapidly absorbed by the diaper and wicked by the diaper. It was also noted that with the passage of time, fluid was being re-absorbed by the auxiliary absorbent article as shown by the arrows thus making use of the absorbent capacity of the auxiliary absorbent article in area 60 remote from the initial wetting of the auxiliary absorbent article. These observations correlate with the test results achieved which indicate that with the use of the

TABLE

| DIAPER TYPE TESTED | | I DIAPER GRAMS | II UNDER PAD GRAMS | III BOOSTER PAD TESTED | IV BOOSTER GRAMS | V FLUID INTRODUCED | VI CAPACITY |
|---|---|---|---|---|---|---|---|
| Commercial Diaper | Net Weight | 209.67 | 17.03 | | | 180 CC | |
| | Dry Weight | 37.67 | 10.05 | | | | |
| | Total Increase In Weight | 172.00 | 6.98 | | — | | 164.92 GMS |
| Commercial Diaper | Net Weight | 202.00 | 27.56 | Revco | 106.0 | 270 CC | |
| | Dry Weight | 38.07 | 10.02 | Diaper | 17.25 | | |
| | Total Increase In Weight | 163.93 | 17.54 | Doublers | 88.75 | | 235.2 GMS |
| Commercial Diaper | Net Weight | 237.90 | 16.11 | Auxiliary | 73.5 | 270 CC | |
| | Dry Weight | 37.15 | 10.04 | Absorbent | 9.0 | | |
| | Total Increase In Weight | 200.75 | 6.07 | Article | 64.5 | | 259.15 GMS |

As may be noted in the chart, the auxiliary absorbent article of the present invention increases the overall absorbent capacity of the diaper listed in the last column of the table. As may also be noted in Column I, the flow through abilities of the auxiliary absorbent article of the present invention allow the underlying absorbent article auxiliary absorbent article according to the present invention, full absorbent capacity of the underlying diaper is used. However, with the use of the Revco Booster Pad, full absorbent capacity of the underlying diaper is not achieved.

FIG. 5 illustrates schematically a preferred embodiment of the auxiliary absorbent article according to the present invention. In FIG. 5, the diaper is shown at 70 and the T-shaped auxiliary absorbent article disposed upon the diaper at 72 or alternatively at 74. In this particular embodiment of the auxiliary absorbent article, the article is shaped to maximize the absorbent capacity of the auxiliary absorbent article for use in diapering a male or female child. The orientation of the diaper is shown by the location of the tape tabs 76 along the back waistband portion as is common in commercial diapers. When the auxiliary absorbent article is disposed on the diaper as at 72, it provides the maximum enhanced absorbent capacity for use with a female child. When the auxiliary absorbent article is disposed as shown at 74, the maximum enhanced absorbent capacity is achieved when the diaper and auxiliary absorbent article are worn by a male infant. T-shaped disposable diapers are disclosed in U.S. Pat. No. 3,768,479.

The foregoing description and drawings are illustrative but are not to be taken as limiting. Other variations and modifications are possible without departing from the spirit and scope of the present invention.

I claim:

1. An auxiliary absorbent article for use atom a primary absorbent article having absorbent capacity and wicking ability, said auxiliary absorbent article enhancing the absorptive capacity of the primary absorbent article, said auxiliary absorbent article comprising a superabsorbent layer, an upper facing layer, and an undersurface, said superabsorbent layer comprising a superabsorbent material dispersed in a matrix such that fluid passes through said auxiliary absorbent article and may be absorbed by the primary absorbent article, wicked along the undersuface of the auxiliary absorbent article, and absorbed through the undersurface of the super-absorbent layer in remote regions from the initial wetting of the auxiliary absorbent article whereby the full absorbent capacity of the primary absorbent article may be utilized.

2. An auxiliary absorbent article as in claim 1 wherein said article is T-shaped.

3. An auxiliary absorbent article as in claim 1 with intermittent adhesive disposed on the undersurface thereof for fastening to the primary absorbent article.

4. An auxiliary absorbent article as in claim 3 wherein said superabsorbent layer comprises a superabsorbent material in a tissue layer.

5. An auxiliary absorbent article as in claim 3 wherein said facing layer encircles said superabsorbent layer and forms the undersurface of the auxiliary absorbent article.

6. In combination, a primary absorbent article and an auxiliary absorbent article, said auxiliary absorbent article contributing to the overall absorbent capacity of the combination while not interfering with the absorption characteristics of the primary absorbent article, said primary absorbent article having absorbent capacity and wicking ability, and said auxiliary absorbent article comprising an upper facing layer, a superabsorbent layer and an undersurface in juxtaposition with the primary absorbent article, said superabsorbent layer comprising a superabsorbent material dispersed in a matrix such that fluid passes through said facing and superabsorbent layers and is absorbed by the primary absorbent article, and wicked along the undersurface thereof and absorbed through the undersurface of the superabsorbent layer in remote regions of the initial wetting of the auxiliary absorbent article whereby the full absorbent capacity of the primary absorbent article may be utilized.

* * * * *

UNITED STATES PATENT AND TRADEMARK OFFICE
CERTIFICATE OF CORRECTION

PATENT NO. : 4,938,756

DATED : July 3, 1990

INVENTOR(S) : JoAnn E. Salek

It is certified that error appears in the above-identified patent and that said Letters Patent is hereby corrected as shown below:

Claim 1, column 5, line 25: "use atom" should be --use atop--.

Signed and Sealed this

Sixth Day of October, 1992

Attest:

DOUGLAS B. COMER

Attesting Officer

Acting Commissioner of Patents and Trademarks